United States Patent
Hou et al.

(10) Patent No.: US 11,053,259 B2
(45) Date of Patent: Jul. 6, 2021

(54) CRYSTAL OF CEPHALOSPORIN INTERMEDIATE 7α-METHOXY CEPHALOTHIN AND METHOD FOR PREPARING SAME

(71) Applicant: QILU ANTIBIOTICS PHARMACEUTICAL CO. LTD., Jinan (CN)

(72) Inventors: Chuanshan Hou, Jinan (CN); Fei Tang, Jinan (CN); Meiju Fan, Jinan (CN); Xin Wang, Jinan (CN); Jinglong Fu, Jinan (CN); Michao Shi, Jinan (CN); Xi Lei, Jinan (CN); Hongmei Xu, Jinan (CN)

(73) Assignee: QILU ANTIBIOTICS PHARMACEUTICAL CO. LTD., Jinan (CN)

( * ) Notice: Subject to any disclaimer, the term of this patent is extended or adjusted under 35 U.S.C. 154(b) by 0 days.

(21) Appl. No.: 16/494,276

(22) PCT Filed: Feb. 23, 2018

(86) PCT No.: PCT/CN2018/077000
§ 371 (c)(1),
(2) Date: Sep. 13, 2019

(87) PCT Pub. No.: WO2018/177048
PCT Pub. Date: Oct. 4, 2018

(65) Prior Publication Data
US 2020/0131197 A1    Apr. 30, 2020

(30) Foreign Application Priority Data
Apr. 1, 2017 (CN) .......................... 201710214602.0

(51) Int. Cl.
*C07D 501/34* (2006.01)

(52) U.S. Cl.
CPC ........ *C07D 501/34* (2013.01); *C07B 2200/13* (2013.01)

(58) Field of Classification Search
CPC .................................................. C07D 501/34
USPC ........................................................ 540/219
See application file for complete search history.

(56) References Cited

U.S. PATENT DOCUMENTS 3,962,231 A * 6/1976 Pines ................... C07D 501/04
540/217

\* cited by examiner

*Primary Examiner* — Kahsay Habte
(74) *Attorney, Agent, or Firm* — CBM Patent Consulting, LLC

(57) ABSTRACT

The present invention relates to a crystal of cephalosporin intermediate 7α-methoxy cephalothin (I) and a method for preparing same. The crystal of 7α-methoxy cephalothin (I) undergoes Cu-Kα radiation and X-ray powder diffraction expressed in terms of angle 2θ; the crystal of 7α-methoxy cephalothin (I) has characteristic absorption peaks at positions of 7.34°±0.20°, 12.71°±0.20°, 14.25°±0.20°, 14.68°±0.20°, 16.52°±0.20°, 17.99°±0.20°, 19.98°±0.20°, and 22.69°±0.20°. The crystal of 7α-methoxy cephalothin provided by the present invention is easy to prepare. Related test data shows that the crystal of 7α-methoxy cephalothin has high purity, low impurity content, and good stability. The preparation cost is low, the preparation method is simple to operate, conditions are mild and easy to control, and crystals of 7α-methoxy cephalothin can be obtained stably. The invention is applicable to industrial production.

10 Claims, 1 Drawing Sheet

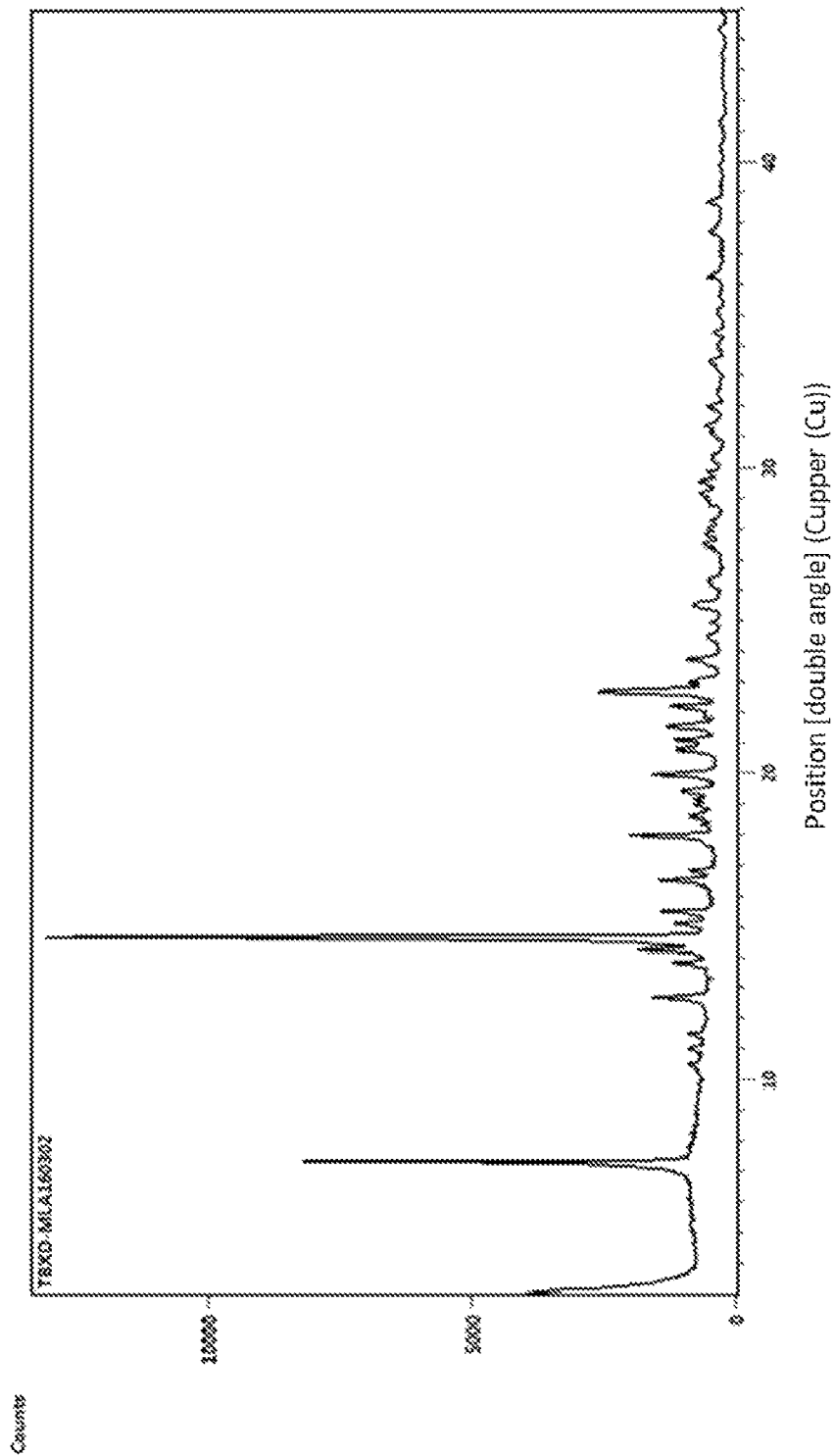

CRYSTAL OF CEPHALOSPORIN INTERMEDIATE 7α-METHOXY CEPHALOTHIN AND METHOD FOR PREPARING SAME

TECHNICAL FIELD OF THE DISCLOSURE

The present invention belongs to the field of drug synthesis and relates to a crystal of cephalosporin intermediate and a method for preparing same, in particular to the crystal of 7α-methoxy cephalothin and the method for preparing same.

BACKGROUND

The full name of 7α-methoxy cephalothin (I) is (6R,7S)-3-acetyloxymethyl-7-methoxy-8-oxo-7-[2-(2-thienyl)acetamido]-5-thia-1-nitrobicyclo [4.2.0] oct-2-ene-2-carboxylic acid. It is an important cephalosporin intermediate and mainly used for synthesis of cefoxitin.

In the existing technology, 7α-methoxy cephalothin is separated in the form of cyclohexylamine salt, as shown in formula II. The following preparation process is disclosed in U.S. Pat. No. 7,662,955: Cephalothin is put into a mixed solvent of dichloromethane and methanol for methoxylation reaction at −90° C., to produce 7α-methoxy cephalothin; after quenching and acid extraction, dichloromethane solution of 7α-methoxy cephalothin is obtained, concentrated and then added with cyclohexylamine to separate out its cyclohexylamine salt.

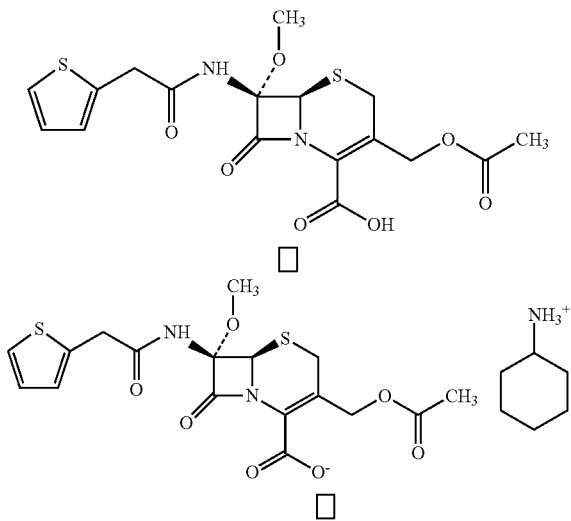

The existing technology of separating 7α-methoxy cephalothin in the form of cyclohexylamine salt has the following disadvantages: firstly, due to poor atom economy of the process of 7α-methoxy cephalothin, the additional use of cyclohexylamine obviously leads to an increase in cost, without any contribution to the structure of the final product cefoxitin; secondly, cyclohexylamine may remain in the final product, thus posing additional quality risks; thirdly, with strong hygroscopicity and poor storage stability, the cyclohexylamine salt is not the best choice for practical application in industrial production; finally, the separation of cyclohexylamine salt and the use of cyclohexylamine salt in the next step need to consider the recovery, purification and recycling of cyclohexylamine to lower the cost and reduce environmental pollution, thereby increasing the complexity of the overall process.

No report on the crystal of 7α-methoxy cephalothin and the method for preparing same is seen in the existing technology.

SUMMARY OF THE DISCLOSURE

Against the disadvantages of the existing technology, one object of the present invention is to provide a crystal of cephalosporin intermediate, i.e. the crystal of 7α-methoxy cephalothin, another object of the present invention is to provide the method for preparing the crystal of α-methoxy cephalothin.

The technical solution of the present invention is:

The crystal of cephalosporin intermediate 7α-methoxy cephalothin undergoes Cu-Kα radiation and X-ray powder diffraction expressed in terms of angle 2θ; the said crystal of 7α-methoxy cephalothin has characteristic absorption peaks at positions of 7.34°±0.20°, 12.71°±0.20°, 14.25°±0.20°, 14.68°±0.20°, 16.52°±0.20°, 17.99°±0.20°, 19.98°±0.20°, and 22.69°±0.20°.

According to a preferred embodiment of the present invention, after undergoing Cu-Kα radiation and X-ray powder diffraction expressed in terms of angle 2θ, the said crystal of 7α-methoxy cephalothin has characteristic absorption peaks at positions of 7.34°, 12.71°, 13.84°, 14.25°, 14.68°, 15.14°, 15.51°, 16.52°, 16.85°, 17.99°, 19.45°, 19.98°, 20.80°, 21.12°, 21.54°, 22.21°, 22.69°, 22.99°, 23.77° and 25.59°.

According to a further preferred embodiment of the present invention, after undergoing Cu-Kα radiation and X-ray powder diffraction expressed in terms of angle 2θ, the X-ray powder diffraction spectrum of the said crystal of 7α-methoxy cephalothin has characteristic absorption peaks at positions of 7.34°, 10.54°, 11.02°, 11.51°, 12.71°, 13.84°, 14.25°, 14.68°, 15.14°, 15.51°, 16.52°, 16.85°, 17.99°, 18.36°, 18.63°, 18.98°, 19.45°, 19.98°, 20.80°, 21.12°, 21.54°, 22.21°, 22.69°, 22.99°, 23.77°, 24.49°, 24.98°, 25.59°, 26.33°, 27.50°, 27.81°, 28.04°, 28.31°, 29.15°, 29.57°, 29.87°, 30.42°, 31.08°, 31.37°, 31.97°, 33.54°, 34.41°, 36.29°, 37.69° and 38.66°.

According to a still further preferred embodiment of the present invention, the X-ray powder diffraction spectrum diagram of the said crystal of 7α-methoxy cephalothin is as shown in FIG. 1.

A method for preparing the crystal of cephalosporin intermediate 7α-methoxy cephalothin, which is one of the following three methods:

(1) Concentrate and crystalize the organic solution of 7α-methoxy cephalothin under reduced pressure; or (2) Mix the aqueous solution of 7α-methoxy cephalothin of pH 4-10 with acid, and crystalize it; or (3) Dissolve the cyclohexylamine salt of 7α-methoxy cephalothin in water before acidification and crystallization.

According to a preferred embodiment of the present invention, the organic solvent of the organic solution of 7α-methoxy cephalothin in method (1) is selected from one or a combination of dichloromethane or ethyl acetate.

According to a preferred embodiment of the present invention, the said aqueous solution of 7α-methoxy cephalothin in method (2) is prepared in the following way: obtain it after extracting 7α-methoxy cephalothin from its organic solution into the aqueous phase with a base; or obtain it by dissolving crystalline, amorphous or oily 7α-methoxy cephalothin in water with a base;

According to a further preferred embodiment of the present invention, the said organic solvent of the organic solution is selected from one or a combination of dichloromethane or ethyl acetate; the said base is selected from one or a combination of ammonia water, sodium hydroxide, sodium bicarbonate, sodium carbonate, potassium hydroxide, potassium carbonate, potassium bicarbonate or triethylamine.

According to a preferred embodiment of the present invention, the said acid in method (2) or (3) is selected from one or a combination of hydrochloric acid, sulfuric acid, phosphoric acid, formic acid, acetic acid or methanesulfonic acid.

According to a preferred embodiment of the present invention, when the crystal of 7α-methoxy cephalothin is prepared by the said method in the present invention, the seed crystals may or may not be added. The seed crystals can be prepared with reference to relevant embodiments of the present invention, such as Embodiment 1.

According to a further preferred embodiment of the present invention, the method for preparing the crystal of cephalosporin intermediate 7α-methoxy cephalothin is one of the following three methods:

(1) Concentrate 1064 g of dichloromethane solution containing about 85.7 g of 7α-methoxy cephalothin to 365 g under reduced pressure, crystallize for 180 min, further concentrate it to 200 g, cool it down to 0-5° C., filter, wash and dry it to obtain 7α-methoxy cephalothin;

(2) Add aqueous solution of sodium bicarbonate with a mass concentration of 7% into 1050 g of dichloromethane solution containing 85.2 g of 7α-methoxy cephalothin until the pH reaches 7.0, leave it for delamination, discard the organic phase, and obtain the aqueous phase, which is the aqueous solution of 7α-methoxy cephalothin; add hydrochloric acid to the aqueous solution to adjust the pH to 3.0, add the seed crystals and crystallize for 30 min, continue to add hydrochloric acid to adjust the pH to 2.0, cool it down to 0-5° C., filter, wash and dry it to obtain 7α-methoxy cephalothin;

(3) Dissolve 100.0 g of cyclohexylamine salt of 7α-methoxy cephalothin in 300 ml of water, add 3 mol/L sulfuric acid to adjust the pH to 3.0, separate crystals out, crystallize for 30 min, continue to add 3 mol/L sulfuric acid to adjust the pH to 2.0, cool it down to 0-5° C., filter and dry it to obtain 7α-methoxy cephalothin The dichloromethane solution containing 7α-methoxy cephalothin and the cyclohexylamine salt of 7α-methoxy cephalothin in the preparation method of the present invention can be prepared with reference to U.S. Pat. No. 7,662,955.

The beneficial effects of the present invention over the existing technology are as follows:

1. The crystal of 7α-methoxy cephalothin provided by the present invention is easy to prepare. Related test data shows that the crystal of 7α-methoxy cephalothin has high purity, low impurity content, and good stability.

2. The crystal of 7α-methoxy cephalothin provided by the present invention has significantly improved quality stability compared with its cyclohexylamine salt, and is more suitable for industrial production, transportation, storage and application.

3. The preparation method involved in the present invention no longer uses cyclohexylamine, thus saving cost of material; it's not necessary to consider the recovery of cyclohexylamine, which is beneficial to reducing the pressure for environmental protection and process complexity; and the products don't have quality risks posed by cyclohexylamine residue.

4. The solvent required for the preparation method involved in the present invention is a conventional solvent. The preparation cost is low, the preparation method is simple to operate, conditions are mild and easy to control, and crystals of 7α-methoxy cephalothin can be obtained stably. The invention is applicable to industrial production.

BRIEF DESCRIPTION OF THE FIGURES

FIG. 1 is an X-ray powder diffraction pattern of the crystal of 7α-methoxy cephalothin in Embodiment 1.

DETAILED DESCRIPTION

The present invention is further described in combination with the embodiments as follows, but the protection scope of the present invention is not limited to this.

Basis of X-ray powder diffraction test: General Rule 0451—The Second Method of Chinese Pharmacopoeia 2015 Edition.

Test instrument: PANalytical X-ray powder diffractometer (model: X'Pert PRO MPD).

Test method: The target material is copper, the light tube is set to 40 KV and 40 mA, the diffraction mode is reflection, and the scanning mode is continuous; the divergence slit is 1/8°, the anti-scatter slit is 1/4°, and the scanning range is 3-45°, the scanning step size is 0.026°, and the scanning speed is 8°/min.

Embodiment 1

Prepare and obtain 1064 g of dichloromethane solution containing about 85.7 g of 7α-methoxy cephalothin with reference to U.S. Pat. No. 7,662,955, concentrate it to 365 g under reduced pressure, crystallize for 180 min, further concentrate it to 200 g, cool it down to 0-5° C., filter, wash and dry it to obtain 7α-methoxy cephalothin;

The X-ray powder diffraction spectrum of the 7α-methoxy cephalothin obtained is shown in FIG. 1.

Embodiment 2

Prepare and obtain 1070 g dichloromethane solution containing about 84.9 g of 7α-methoxy cephalothin with reference to U.S. Pat. No. 7,662,955, add 7% aqueous solution of sodium bicarbonate until the pH reaches 7.0, leave it for delamination, and discard the organic phase. Add 500 ml of ethyl acetate into the aqueous phase and adjust the pH to 2.0 with 6 mol/L hydrochloric acid, leave it for delamination, and the organic phase is an ethyl acetate solution of 7α-methoxy cephalothin. Concentrate the solution to 250 g under reduced pressure, add seed crystals, crystallize for 30 min, separate crystals out, continue to concentrate it to 180 g, cool it down to 0-5° C., filter and dry it to obtain 78.7 g of 7α-methoxy cephalothin.

The X-ray powder diffraction pattern is substantially identical to FIG. 1.

Embodiment 3

Prepare and obtain 1050 g dichloromethane solution containing 85.2 g of 7α-methoxy cephalothin with reference to U.S. Pat. No. 7,662,955, add 7% aqueous solution of sodium bicarbonate until the pH reaches 7.0, leave it for delamination, discard the organic phase, and obtain the aqueous phase, which is an aqueous solution of 7α-methoxy cephalothin of pH 7.0. Add hydrochloric acid to the aqueous solution to adjust the pH to 3.0, add the seed crystals and crystallize for 30 min, continue to add hydrochloric acid to adjust the pH to 2.0, cool it down to 0-5° C., filter, wash and dry it to obtain 79.4 g of 7α-methoxy cephalothin;

The X-ray powder diffraction pattern is substantially identical to FIG. 1.

Embodiment 4

A preparation method as described in Embodiment 3 except that the pH is adjusted to 4.0 with an aqueous solution of sodium bicarbonate before delamination. It is finally filtered but not dried to obtain 71.7 g of wet 7α-methoxy cephalothin.

A little wet product is taken and dried for diffraction experiment, and the remaining wet product is directly used for the synthesis of cefoxitin in the next step.

The X-ray powder diffraction pattern is substantially identical to FIG. 1.

Embodiment 5

A preparation method as described in Embodiment 3 except that the pH is adjusted to 10.0 with an aqueous solution of potassium carbonate before delamination and 79.5 g of 7α-methoxy cephalothin is finally obtained.

The X-ray powder diffraction pattern is substantially identical to FIG. 1.

Embodiment 6

A preparation method as described in Embodiment 3 except that the aqueous phase obtained by delamination is dropped into 110 ml of 2 mol/L aqueous solution of formic acid, crystallized for 30 min, further added with hydrochloric acid to adjust the pH to 2.0, cooled down to 0-5° C., filtered, washed and dried to obtain 78.9 g of 7α-methoxy cephalothin.

The X-ray powder diffraction pattern is substantially identical to that of FIG. 1.

Embodiment 7

Prepare and obtain 100.0 g of cyclohexylamine salt of 7α-methoxy cephalothin with reference to U.S. Pat. No. 7,662,955, dissolve it in 300 ml of water, add 3 mol/L sulfuric acid to adjust the pH to 3.0, separate crystals out, crystallize for 30 min, continue to add 3 mol/L sulfuric acid to adjust the pH to 2.0, cool it down to 0-5° C., filter and dry it to obtain 70.4 g of 7α-methoxy cephalothin.

The X-ray powder diffraction pattern is substantially identical to FIG. 1.

Embodiment 8

Uniformly mix 200 ml of 2 mol/L aqueous solution of acetic acid with 10 ml of 6 mol/L hydrochloric acid, add 100.0 g of cyclohexylamine salt of 7α-methoxy cephalothin into it in portions, add seed crystals, crystalize for 30 min, continue to add hydrochloric acid to adjust the pH to 2.0, cool it down to 0-5° C., filter, wash and dry it to obtain 74.9 g of 7α-methoxy cephalothin.

The X-ray powder diffraction pattern is substantially identical to FIG. 1.

Embodiment 9

Prepare dichloromethane solution of 7α-methoxy cephalothin and cyclohexylamine salt of 7α-methoxy cephalothin with reference to U.S. Pat. No. 7,662,955:

Add 100 g of cephalothin sodium into a mixed solvent of 806 ml of dichloromethane and 83 ml of methanol, and cool it down to −20° C., and add 25.3 g of methanesulfonic acid. Cool it down to −90° C., add 60.8 g of N-chlorosuccinimide under the controlled temperature, and then add mixed solution of 30% sodium methoxide solution (337.3 g) and 160 ml of methanol. After completion of the reaction, add 20.6 g of sodium metabisulfite, 150 ml of 80% aqueous solution of acetic acid, and sodium chloride solution (189 g dissolved in 1164 ml of water). Add 23.5 ml of 6N hydrochloric acid at 0° C., and leave it for delamination. Wash the organic phase obtained with water to remove a small amount of methanol therefrom, and obtain about 1070 g of dichloromethane solution of 7α-methoxy cephalothin, which contains about 86 g of 7α-methoxy cephalothin. Concentrate the solution to 500 ml under reduced pressure, add cyclohexylamine until the pH reaches 6.5, and then add isopropyl ether, mix it for 120 min at 0° C., filter it, wash it with acetone and dry it to obtain 101.0 g cyclohexylamine salt of 7α-methoxy cephalothin.

Embodiment 10

The crystal of 7α-methoxy cephalothin prepared in Embodiment 1 and the cyclohexylamine salt of 7α-methoxy cephalothin prepared in Embodiment 9 were subjected to a 6-month accelerated comparative study on stability and the two products were found to differ significantly in the stability of appearance, hygroscopicity and content, as shown in Table 1-2:

TABLE 1

Test Results of Crystal of 7α-Methoxy Cephalothin from Embodiment 1
Stability of Crystal of 7α-Methoxy Cephalothin at 25° C. and RH of 60%

| | Month 0 | Month 1 | Month 2 | Month 3 | Month 6 |
| --- | --- | --- | --- | --- | --- |
| Appearance | Off-white powder | Off-white powder | Off-white powder | Off-white powder | Off-white powder |
| Moisture | 0.26% | 0.27% | 0.27% | 0.29% | 0.28% |
| Content | 98.2% | 98.2% | 98.1% | 98.1% | 97.9% |

After a 6-month accelerated testing on stability of the crystal of 7α-methoxy cephalothin prepared in embodiments 2-8, the results obtained were basically consistent with Table 1.

TABLE 2

Test Results of Cyclohexylamine Salt of 7α-Methoxy Cephalothin
Prepared in Embodiment 9
Stability of Cyclohexylamine Salt of 7α-Methoxy Cephalothin
at 25° C. and RH of 60%

| | Month 0 | Month 1 | Month 2 | Month 3 | Month 6 |
| --- | --- | --- | --- | --- | --- |
| Appearance | Off-white powder | Light yellow powder | Yellow powder | Yellow powder | Earthy yellow powder |

TABLE 2-continued

Test Results of Cyclohexylamine Salt of 7α-Methoxy Cephalothin
Prepared in Embodiment 9
Stability of Cyclohexylamine Salt of 7α-Methoxy Cephalothin
at 25° C. and RH of 60%

|  | Month 0 | Month 1 | Month 2 | Month 3 | Month 6 |
| --- | --- | --- | --- | --- | --- |
| Moisture | 0.13% | 0.87% | 1.56% | 1.84% | 2.55% |
| Content | 78.4% | 77.5% | 76.3% | 75.1% | 72.4% |

Conclusion: It can be seen from the above 6-month accelerated comparative study on stability that the crystal of 7α-methoxy cephalothin prepared in Embodiment 1 and the cyclohexylamine salt of 7α-methoxy cephalothin prepared in Embodiment 9 of the present invention differ significantly in the stability of appearance, hygroscopicity and content. The crystal provided by the present invention has better purity and quality stability.

What is claimed is:

1. A crystal of 7α-methoxy cephalothin, characterized in that, after undergoing Cu-Ka radiation and X-ray powder diffraction expressed in terms of angle 2θ, the crystal of 7α-methoxy cephalothin has characteristic absorption peaks at positions of 7.34°±0.20°, 12.71°±0.20°, 14.25°±0.20°, 14.68°±0.20°, 16.52°±0.20°, 17.99°±0.20°, 19.98°±0.20°, and 22.69°±0.20°; wherein purity of the crystal of 7α-methoxy cephalothin is up to 98%.

2. The crystal of 7α-methoxy cephalothin according to claim 1, characterized in that, after undergoing Cu-Ka radiation and X-ray powder diffraction expressed in terms of angle 2θ, the crystal of 7α-methoxy cephalothin has characteristic absorption peaks at positions of 7.34°, 12.71°, 13.84°, 14.25°, 14.68°, 15.14°, 15.51°, 16.52°, 16.85°, 17.99°, 19.45°, 19.98°, 20.80°, 21.12°, 21.54°, 22.21°, 22.69°, 22.99°, 23.77° and 25.59°.

3. The crystal of 7α-methoxy cephalothin according to claim 1 or 2, characterized in that, after undergoing Cu-Ka radiation and X-ray powder diffraction expressed in terms of angle 2θ, the crystal of 7α-methoxy cephalothin has characteristic absorption peaks at positions of 7.34°, 10.54°, 11.02°, 11.51°, 12.71°, 13.84°, 14.25°, 14.68°, 15.14°, 15.51°, 16.52°, 16.85°, 17.99°, 18.36°, 18.63°, 18.98°, 19.45°, 19.98°, 20.80°, 21.12°, 21.54°, 22.21°, 22.69°, 22.99°, 23.77°, 24.49°, 24.98°, 25.59°, 26.33°, 27.50°, 27.81°, 28.04°, 28.31°, 29.15°, 29.57°, 29.87°, 30.42°, 31.08°, 31.37°, 31.97°, 33.54°, 34.41°, 36.29°, 37.69° and 38.66°.

4. The crystal of 7α-methoxy cephalothin according to claim 1, characterized in that, the X-ray powder diffraction spectrum diagram of the crystal of 7α-methoxy cephalothin is as shown in the X-ray powder diffraction pattern of the crystal of 7α-methoxy cephalothin.

5. A method for preparing the crystal of 7α-methoxy cephalothin, according to claim 1, characterized in that, it is one of the following three methods:
   (1) concentrate and crystalize the organic solution of 7α-methoxy cephalothin under reduced pressure; or
   (2) mix the aqueous solution of 7α-methoxy cephalothin of pH 4-10 with acid, and crystalize it; or
   (3) dissolve the cyclohexylamine salt of 7α-methoxy cephalothin in water before acidification and crystallization.

6. The method for preparing the crystal of cephalosporin intermediate 7α-methoxy cephalothin according to claim 5, characterized in that, the organic solvent of the organic solution of 7α-methoxy cephalothin in method (1) is selected from one or a combination of dichloromethane or ethyl acetate.

7. The method for preparing the crystal of 7α-methoxy cephalothin according to claim 5, characterized in that, the aqueous solution of 7α-methoxy cephalothin in method (2) is prepared in the following way: obtain it after extracting 7α-methoxy cephalothin from its organic solution into the aqueous phase with a base; or obtain it by dissolving crystalline, amorphous or oily 7α-methoxy cephalothin in water with a base.

8. The method for preparing the crystal of 7α-methoxy cephalothin according to claim 7, characterized in that, the organic solvent of the organic solution is selected from one or a combination of dichloromethane or ethyl acetate; the base is selected from one or a combination of ammonia water, sodium hydroxide, sodium bicarbonate, sodium carbonate, potassium hydroxide, potassium carbonate, potassium bicarbonate or triethylamine.

9. The method for preparing the crystal of 7α-methoxy cephalothin according to claim 5, characterized in that, the acid in method (2) or (3) is selected from one or a combination of hydrochloric acid, sulfuric acid, phosphoric acid, formic acid, acetic acid or methanesulfonic acid; when the crystal of 7α-methoxy cephalothin is prepared by the method in the present invention, the seed crystals may or may not be added.

10. The method for preparing the crystal of 7α-methoxy cephalothin according to claim 5, characterized in that, it is one of the following three methods:
   (1) concentrate 1064 g of dichloromethane solution containing about 85.7 g of 7α-methoxy cephalothin to 365 g under reduced pressure, crystallize for 180 min, further concentrate it to 200 g, cool it down to 0-5° C., filter, wash and dry it to obtain 7α-methoxy cephalothin;
   (2) add aqueous solution of sodium bicarbonate with a mass concentration of 7% into 1050 g of dichloromethane solution containing 85.2 g of 7α-methoxy cephalothin until the pH reaches 7.0, leave it for delamination, discard the organic phase, and obtain the aqueous phase, which is the aqueous solution of 7α-methoxy cephalothin; add hydrochloric acid to the aqueous solution to adjust the pH to 3.0, add the seed crystals and crystallize for 30 min, continue to add hydrochloric acid to adjust the pH to 2.0, cool it down to 0-5° C., filter, wash and dry it to obtain 7α-methoxy cephalothin;
   (3) dissolve 100.0 g of cyclohexylamine salt of α-methoxy cephalothin in 300 ml of water, add 3 mol/L sulfuric acid to adjust the pH to 3.0, separate crystals out, crystallize for 30 min, continue to add 3 mol/L sulfuric acid to adjust the pH to 2.0, cool it down to 0-5° C., filter and dry it to obtain 7α-methoxy cephalothin.

* * * * *